(12) United States Patent
Ghogh et al.

(10) Patent No.: US 8,641,948 B2
(45) Date of Patent: Feb. 4, 2014

(54) METHOD OF MAKING SOLID DISPERSIONS OF HIGHLY CRYSTALLINE THERAPEUTIC COMPOUNDS

(75) Inventors: Indrajit Ghogh, Parsippany, NJ (US); Jennifer Snyder, Morris Plains, NJ (US); Wei Quin Tong, Basking Ridge, NJ (US); Sudha Vippagunta, Morris Plains, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/423,329

(22) Filed: Mar. 19, 2012

(65) Prior Publication Data

US 2012/0190667 A1 Jul. 26, 2012

Related U.S. Application Data

(63) Continuation of application No. 12/376,692, filed as application No. PCT/US2007/017960 on Aug. 14, 2007, now abandoned.

(60) Provisional application No. 60/822,556, filed on Aug. 16, 2006.

(51) Int. Cl.
*B29C 47/00* (2006.01)
*B29C 67/24* (2006.01)

(52) U.S. Cl.
USPC .................. 264/211; 264/176.1; 264/211.21; 424/465

(58) Field of Classification Search
USPC ........... 424/464, 465; 264/176.1, 211, 211.21
See application file for complete search history.

(56) References Cited

U.S. PATENT DOCUMENTS

| 5,837,714 | A | 11/1998 | Rocco et al. ................. 514/313 |
| 6,706,283 | B1 | 3/2004 | Appel et al. ................. 424/473 |
| 6,872,336 | B2 | 3/2005 | Tanno et al. ....................... 264/7 |
| 7,071,202 | B2 * | 7/2006 | Redkar et al. ................. 514/283 |
| 7,749,521 | B2 | 7/2010 | Martens et al. ................. 424/400 |
| 7,825,118 | B2 | 11/2010 | Honigberg et al. ........... 514/249 |
| 8,268,352 | B2 * | 9/2012 | Vaya et al. ..................... 424/469 |
| 2002/0015730 | A1 | 2/2002 | Hoffmann et al. ............. 424/470 |
| 2002/0061873 | A1 | 5/2002 | Matthews et al. ........ 514/211.08 |
| 2003/0021840 | A1 | 1/2003 | Infeld et al. ..................... 424/452 |

(Continued)

FOREIGN PATENT DOCUMENTS

EP 0 836 475 11/2001
WO WO 85/02767 7/1985

(Continued)

OTHER PUBLICATIONS

Zhu et al. "Controlled Release of Poorly Water-Soluble Drug from Hot-melt Extrudates Containing Acrylic Polymers" Drug Development adn Industrial Pharmacy, (Jun. 2006).*

(Continued)

*Primary Examiner* — Joseph S Del Sole
*Assistant Examiner* — Nahida Sultana
(74) *Attorney, Agent, or Firm* — Carmella O'Gorman

(57) ABSTRACT

A process for preparing solid dispersions of highly crystalline compounds. The highly crystalline or thermally labile therapeutic compounds are processed in an extruder in combination with a solubilizing agent and optionally a plasticizer. The resulting extrudate features the therapeutic compound in an amorphous state. Particularly useful as the solubilizing agents are surfactants such as poloxamers.

6 Claims, 2 Drawing Sheets

(56) References Cited

U.S. PATENT DOCUMENTS

| | | | |
|---|---|---|---|
| 2003/0153608 A1* | 8/2003 | Maegerlein et al. | 514/347 |
| 2003/0166602 A1* | 9/2003 | Szoka, Jr. | 514/44 |
| 2003/0212102 A1 | 11/2003 | Koretke et al. | 514/312 |
| 2004/0077232 A1 | 4/2004 | Ebner et al. | |
| 2004/0138263 A1* | 7/2004 | D'Angio et al. | 514/323 |
| 2005/0058705 A1 | 3/2005 | Remon et al. | 424/464 |
| 2005/0080075 A1 | 4/2005 | Nichols et al. | 514/225.5 |
| 2005/0196421 A1 | 9/2005 | Hunter et al. | 424/423 |
| 2005/0214331 A1 | 9/2005 | Levy | 424/400 |
| 2005/0288481 A1 | 12/2005 | DesNoyer et al. | 428/310 |
| 2006/0034937 A1 | 2/2006 | Patel | 424/497 |
| 2006/0040962 A1 | 2/2006 | Wang et al. | 514/263 |
| 2006/0134219 A1 | 6/2006 | Martens et al. | 424/489 |
| 2006/0246109 A1 | 11/2006 | Hossainy et al. | 424/426 |
| 2007/0009592 A1 | 1/2007 | Remon et al. | 424/464 |
| 2007/0202175 A1 | 8/2007 | Ahmed et al. | 424/484 |
| 2008/0003283 A1* | 1/2008 | Feng et al. | 424/464 |
| 2008/0108636 A1* | 5/2008 | Honigberg et al. | 514/263.22 |
| 2008/0287417 A1 | 11/2008 | Ebner et al. | 514/211.08 |
| 2009/0137552 A1* | 5/2009 | Hoehn et al. | 514/211.08 |
| 2009/0192205 A1 | 7/2009 | Augustijns et al. | 514/384 |
| 2009/0297583 A1 | 12/2009 | Desnoyer et al. | 424/425 |
| 2009/0318519 A2 | 12/2009 | Augustijns et al. | 514/384 |
| 2011/0105497 A1* | 5/2011 | Sudhakar | 514/233.8 |
| 2011/0111006 A1* | 5/2011 | Wong et al. | 424/423 |
| 2012/0052040 A1* | 3/2012 | Hunter et al. | 424/78.3 |
| 2012/0082616 A1* | 4/2012 | Trawick et al. | 424/1.21 |
| 2012/0135944 A1* | 5/2012 | Honigberg et al. | 514/34 |
| 2012/0148576 A1* | 6/2012 | Sharma et al. | 424/133.1 |
| 2012/0183535 A1* | 7/2012 | Buggy et al. | 424/133.1 |
| 2012/0245160 A1* | 9/2012 | Thakur | 514/229.2 |
| 2012/0294930 A1* | 11/2012 | Ren et al. | 424/450 |

FOREIGN PATENT DOCUMENTS

| | | | |
|---|---|---|---|
| WO | WO99/21534 | 5/1999 | |
| WO | WO 2006/048296 | 5/2006 | C07D 498/22 |
| WO | WO 2006/059224 | 6/2006 | |
| WO | WO 2006/059224 A1 | 6/2006 | A61K 9/16 |

OTHER PUBLICATIONS

Baker Perkins: Twin Screw Extruders for phamaceutical Applications pp. 1-3 or see link below: http://www.bakerperkinsgroup.com/content/1/401/twin-screw-extruders-for-pharmaceutical-applications.html, 2012.

Zhu, "Controlled release of a poorly water-soluble drug from hot-melt extrudates containing acrylic polymers", Drug Development and Industrial Pharmacy, 32, 569-583 (2006).

Alazar N. Ghebremeskel, Use of surfactants as plasticizers in preparing solid dispersions of poorly soluble API:. stability testing of selected solid dispersions. Pharmaceutical Research, vol. 23, No. 8, pp. 1928-1936 (2006).

* cited by examiner

METHOD OF MAKING SOLID DISPERSIONS OF HIGHLY CRYSTALLINE THERAPEUTIC COMPOUNDS

This is a continuation of application Ser. No. 12/376,692, filed Feb. 6, 2009, which is a National Phase application of PCT/US2007/017960, filed on Aug. 14, 2007, which claims benefit of Provisional Application No. 60/822,556, filed Aug. 16, 2006.

FIELD OF THE INVENTION

The present invention relates to a method of converting the physical state of a poorly water soluble therapeutic compound, for example, in order to manufacture a solid dispersion. Specifically, the inventive method facilitates the change of a poorly soluble therapeutic compound from a highly crystalline state into an amorphous state.

BACKGROUND OF THE INVENTION

Many poorly water soluble therapeutic compounds exist in a physical state that is highly crystalline. Additionally such high crystalline therapeutic compounds often have high melting points. By converting the physical state of such a therapeutic compound into an amorphous state allows for both greater solubility and faster dissolution of the therapeutic compound. This, thus, may increase the bioavailability of the drug.

Various methods have been used to achieve an amorphous state that results in the therapeutic compound being molecularly dispersed in an inert carrier, typically a polymer. Such methods include solvent evaporation, spray drying, and melt fusion. Not all of these processes are ideal for converting the highly crystalline therapeutic compound into an amorphous state. Some methods may result in a product that reverts back, or recrystallizes, into a crystalline state. Other methods utilize organic solvents which may not be desirable due to environmental and safety reasons.

Of particular interest is melt extrusion which uses a twin screw extruder to combine a therapeutic compound with an inert carrier to form a solid dispersion. Typically, the twin screw extruder is heated to facilitate mixing of the therapeutic compound with the carrier. Sometimes heating a melt extruder to a temperature above the melting point of a therapeutic compound may not be suitable since that temperature could exceed the melting point of the carrier, thus causing the carrier to decompose. Additionally, some therapeutic compounds may decompose when melted.

Thus, there is a need for a process that allows for the use of melt extrusion to convert the physical state of a therapeutic compound from being highly crystalline to amorphous that is particularly appropriate for therapeutic compounds that have either a high melting point and/or an attribute of decomposing near or at its melting point. This invention addresses such a need by utilizing a melt extrusion process that incorporates a solubilizing agent. This solubilizing agent allows the processing temperature for a therapeutic compound to be lowered in order to preserve the integrity of the therapeutic compound while allowing for the physical state of the therapeutic compound to change from crystalline to amorphous. Furthermore, having such a process expands the formulation possibilities, as carriers or polymers that would normally decompose at high temperatures may be subsequently used providing greater flexibility for the pharmaceutical formulator.

SUMMARY OF THE INVENTION

Featured in the present invention is a method for making a solid dispersion which is particularly usefully for high melting point (i.e., greater than or equal to 200° C.) therapeutic compounds and/or therapeutic compounds that are thermally labile. The process comprises the steps of combining such a therapeutic compound with a carrier and a solubilizing agent to form a mixture; subsequently processing the mixture in an extruder with heat, and extruding the mixture to form an extrudate. During processing in the melt extruder, the solubilizing agent facilitates the conversion of the physical state of the therapeutic compound from being crystalline to amorphous, at a reduced processing temperature. This conversion to an amorphous state allows for the formation of a solid dispersion that comprises the formerly crystalline therapeutic compound.

In a further embodiment of the present invention, the process uses a poloxamer, especially poloxamer 188 as the solubilizing agent. The melt extruder is heated from a temperature of 50° C. to 175° C. or more particularly, 150° C. to 170° C.

BRIEF DESCRIPTION OF THE DRAWINGS

The accompanying drawings, which are incorporated in and constitute a part of the specification, illustrate an exemplary embodiment of the present invention.

DETAILED DESCRIPTION OF THE INVENTION

Figure 1:
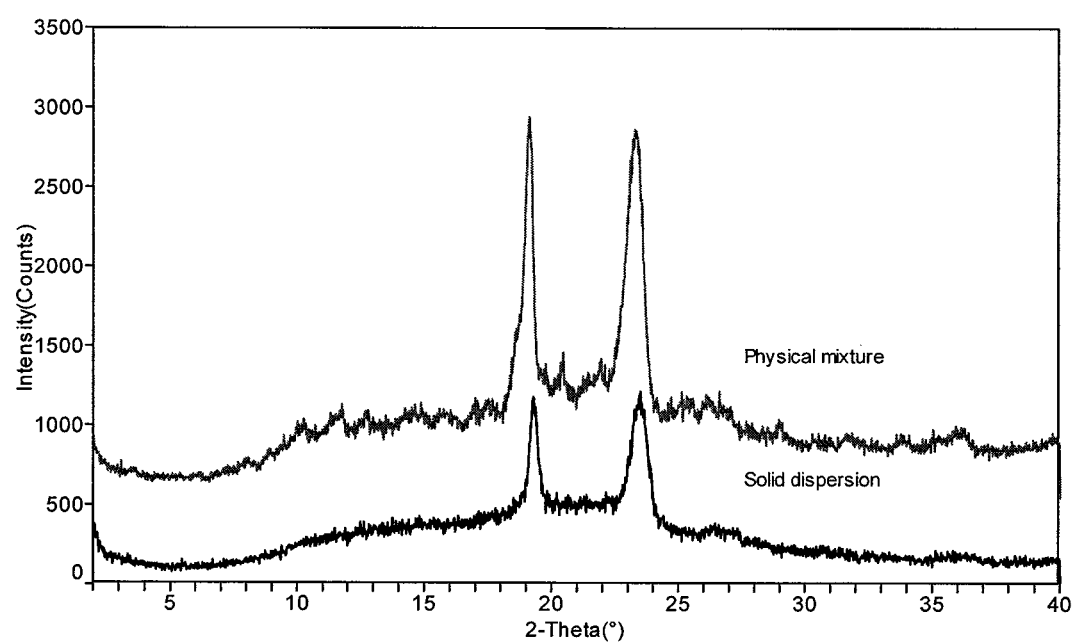
FIG. 1 depicts a chart showing two powder x-ray diffraction patterns of a physical mixture of the exemplary constituents in Table 2 as compared to a solid dispersion of the same constituents.

The present invention relates to a melt extrusion process of making a solid dispersion of a high melting point, crystalline and/or thermally labile poorly soluble therapeutic compound in an inert carrier with a solubilizing agent by using a melt extruder, for example a twin screw extruder. Particularly useful as the solubilizing agents are block copolymers, for example, non-ionic synthetic block copolymers of ethylene oxide and propylene oxide, i.e., poloxamer. Alternatively, solubilizing agents may also include other surfactants in addition to the aforementioned class of block copolymers.

As used herein the term "pharmaceutical composition" means a mixture containing a therapeutic compound to be administered to a mammal, e.g., a human, in order to prevent, treat or control a particular disease or condition affecting the mammal.

As used herein the term "pharmaceutically acceptable" refers to those compounds, materials, compositions and/or dosage forms, which are, within the scope of sound medical judgment, suitable for contact with the tissues of mammals, especially humans, without excessive toxicity, irritation, allergic response and other problem complications commensurate with a reasonable benefit/risk ratio.

As used herein the term "therapeutic compound" means any compound, substance, drug, medicament, or active ingredient having a therapeutic or pharmacological effect, and which is suitable for administration to a mammal, e.g., a human, in a composition that is particularly suitable for oral administration.

As used herein the term "poorly soluble" refers to slightly soluble or very slightly soluble as defined by the U.S. Pharmacopoeia, e.g., from about 100 to 10,000 parts of solvent required for one part of solute.

As used herein the term "crystalline" or "crystalline form" means having a physical state that is a regular three-dimensional array of atoms, ions, molecules or molecular assemblies. Crystalline forms have lattice arrays of building blocks called asymmetric units that are arranged according to well-defined symmetries into unit cells that are repeated in three-dimensions. In contrast, the term "amorphous" or "amorphous form" refers to an unorganized (no orderly) structure. The physical state of a therapeutic compound may be determined by exemplary techniques such as x-ray diffraction, polarized light microscopy and/or differential scanning calorimetry.

As used herein the term "thermally labile" therapeutic compound refers to a therapeutic compound which undergoes spontaneous degradation or decomposition when the therapeutic compound is heated at, above or near its melting point.

As used herein, the term "high melting point" refers to a melting point or the lowest point in a melting range that is greater than or equal to 200° C.

Examples of therapeutic classes of therapeutic compounds include, but are not limited to, antacids, anti-inflammatory substances, coronary dilators, cerebral dilators, peripheral vasodilators, anti-infectives, psychotropics, antimanics, stimulants, antihistamines, anti-cancer therapeutic compounds, laxatives, decongestants, vitamins, gastrointestinal sedatives, antidiarrheal preparations, anti-anginal therapeutic compounds, vasodilators, antiarrythmics, anti-hypertensive therapeutic compounds, vasoconstrictors and migraine treatments, anticoagulants and antithrombotic therapeutic compounds, analgesics, anti-pyretics, hypnotics, sedatives, anti-emetics, anti-nauseants, anti-convulsants, neuromuscular therapeutic compounds, hyper- and hypoglycemic agents, thyroid and anti-thyroid preparations, diuretics, anti-spasmodics, uterine relaxants, mineral and nutritional additives, anti-obesity therapeutic compounds, anabolic therapeutic compounds, erythropoietic therapeutic compounds, anti-asthmatics, expectorants, cough suppressants, mucolytics, anti-uricemic therapeutic compounds, and therapeutic compounds or substances acting locally in the mouth.

The therapeutic compound(s) is (are) present in the pharmaceutical compositions of the present invention in a therapeutically effective amount or concentration. Such a therapeutically effective amount or concentration is known to one of ordinary skill in the art as the amount or concentration varies with the therapeutic compound being used and the indication which is being addressed. For example, in accordance with the present invention, the therapeutic compound may be present in an amount by weight of about 0.05% to about 99% weight of pharmaceutical composition. In one embodiment, the therapeutic compound may be present in an amount by weight of about 10% to about 95% by weight of the pharmaceutical composition.

As used herein the term "carrier" refers to a pharmaceutically acceptable matrix suitable for forming a solid or molecular dispersion of the therapeutic compound. Particularly useful as carriers are polymers or mixtures of polymers. Types of polymers include, but are not limited to, water-soluble, water-swellable, water insoluble polymers and combinations of the foregoing.

Examples of polymers include, but are not limited to:

homopolymers and copolymers of N-vinyl lactams, e.g., homopolymers and copolymers of N-vinyl pyrrolidone (e.g., polyvinylpyrrolidone), copolymers of N-vinyl pyrrolidone and vinyl acetate or vinyl propionate;

cellulose esters and cellulose ethers (e.g., methylcellulose and ethylcellulose) hydroxyalkylcelluloses (e.g., hydroxypropylcellulose), hydroxyalkylalkylcelluloses (e.g., hydroxypropylmethylcellulose), cellulose phthalates (e.g., cellulose acetate phthalate and hydroxylpropylmethylcellulose phthalate) and cellulose succinates (e.g., hydroxypropylmethylcellulose succinate or hydroxypropylmethylcellulose acetate succinate);

high molecular polyalkylene oxides such as polyethylene oxide and polypropylene oxide and copolymers of ethylene oxide and propylene oxide;

polyacrylates and polymethacrylates (e.g., methacrylic acid/ethyl acrylate copolymers, methacrylic acid/methyl methacrylate copolymers, butyl methacrylate/2-dimethylaminoethyl methacrylate copolymers, poly(hydroxyalkyl acrylates), poly(hydroxyalkyl methacrylates));

polyacrylamides;

vinyl acetate polymers such as copolymers of vinyl acetate and crotonic acid, partially hydrolyzed polyvinyl acetate;

polyvinyl alcohol; and oligo- and polysaccharides such as carrageenans, galactomannans and xanthan gum, or mixtures of one or more thereof.

Particular useful carriers are those with low glass transition temperatures (i.e., $T_g$). Examples of carriers with low glass transition temperatures include but are not limited to PVP K30, PVP K17, and PVP/VA.

Along with the polymer, the carrier may contain other pharmaceutically acceptable ingredients, for example plasticizers.

As used herein, the term "plasticizer" refers to a material that may be incorporated into the pharmaceutical composition in order to decrease the glass transition temperature and the melt viscosity of a polymer by increasing the free volume between polymer chains. Plasticizers, for example, include, but are not limited to, water; citrate esters (e.g., triethylcitrate, triacetin); low molecular weight poly(alkylene oxides) (e.g., poly(ethylene glycols), poly(propylene glycols), poly(ethylene/propylene glycols)); glycerol, pentaerythritol, glycerol monoacetate, diacetate or triacetate; propylene glycol; sodium diethyl sulfosuccinate; and the therapeutic compound itself. The plasticizer can be present in concentration from about 0% to 15%, e.g., 0.5% to 5% by weight of the pharmaceutical composition. Examples of plasticizers can also be found in *The Handbook of Pharmaceutical Additives*, Ash et al., Gower Publishing (2000).

As used herein, the term "solubilizer" refers to a material able to solubilize or partially solubilize the therapeutic compound and/or polymer. Particularly useful as solubilizers are surfactants. The term "surfactant" as used herein may include non-ionic surfactants, anionic surfactants, and the like, and suitable combinations of two or more thereof.

Particularly useful as a solubilizer are water-soluble, non-ionic synthetic block copolymers, such as polyoxyethylene-polyoxypropylene block copolymers. The generic term for such copolymers is poloxamer. As used herein, the term "a poloxamer" refers to at least one polymer having the formula: $HO(C_2H_4)_a(C_3H_6O)_b(C_2H_4O)_aH$ in which "a" and "b" denote the number of polyoxyethylene and polyoxypropylene units, respectively. Examples of poloxamers are shown in the following Table 1 with their respective "a" and "b" values for inserting into the aforementioned formula:

TABLE 1

| | | |
|---|---|---|
| poloxamer 105 | a = 11 | b = 16 |
| poloxamer 108 | a = 46 | b = 16 |
| poloxamer 122 | a = 5 | b = 21 |
| poloxamer 123 | a = 7 | b = 21 |
| poloxamer 124 | a = 11 | b = 21 |
| poloxamer 181 | a = 3 | b = 30 |
| poloxamer 182 | a = 8 | b = 30 |

TABLE 1-continued

| | | |
|---|---|---|
| poloxamer 183 | a = 10 | b = 30 |
| poloxamer 184 | a = 13 | b = 30 |
| poloxamer 185 | a = 19 | b = 30 |
| poloxamer 188 | a = 75 | b = 30 |
| poloxamer 212 | a = 8 | b = 35 |
| poloxamer 215 | a = 24 | b = 35 |
| poloxamer 217 | a = 52 | b = 35 |
| poloxamer 231 | a = 16 | b = 39 |
| poloxamer 234 | a = 22 | b = 39 |
| poloxamer 235 | a = 27 | b = 39 |
| poloxamer 237 | a = 62 | b = 39 |
| poloxamer 238 | a = 97 | b = 39 |
| poloxamer 282 | a = 10 | b = 47 |
| poloxamer 284 | a = 21 | b = 47 |
| poloxamer 288 | a = 122 | b = 47 |
| poloxamer 331 | a = 7 | b = 54 |
| poloxamer 333 | a = 20 | b = 54 |
| poloxamer 334 | a = 31 | b = 54 |
| poloxamer 335 | a = 38 | b = 54 |
| poloxamer 338 | a = 128 | b = 54 |
| poloxamer 401 | a = 6 | b = 67 |
| poloxamer 402 | a = 13 | b = 67 |
| poloxamer 403 | a = 21 | b = 67 |
| poloxamer 407 | a = 98 | b = 67 |

An example of a particularly useful poloxamer is poloxamer 188 which is commercially available as PLURONIC F68 from BASF (Mt. Olive, N.J.).

As used herein, the term "melt granulating" refers to an exemplary process to form a molecular dispersion of the once highly crystalline and/or thermally labile therapeutic compound. The processing is accomplished by the use of an extruder.

In general, an extruder includes a rotating screw(s) within a stationary barrel with an optional die located at one end of the barrel. Along the entire length of the screw, distributive mixing of the materials (e.g., the therapeutic compound, release retardant, and any other needed excipients) is provided by the rotation of the screw(s) within the barrel. Conceptually, the extruder can be divided into three sections: a feeding section; a heating section and a metering section. In the feeding section, the raw materials are fed into the extruder, e.g. from a hopper. The raw materials can be directly added to the hopper without the need of a solvent. In the heating section, the raw materials are heated to a particular temperature necessary for processing. The processing temperature does not exceed the degradation temperature of the materials. For example, poloxamer 188 has a degradation temperature of 175° C. The processing temperature can range from about 50° C. to about 175° C., e.g., 150° C. to about 170° C. After the heating section is a metering section in which the mixed materials are optionally extruded through a die into a particular shape. Types of extruders particularly useful in the present invention are single- and twin-screw extruders. Such equipment and techniques used to make pharmaceutical composition by extrusion have been established and are well-known in the prior art. See, e.g., Jorg Breitenbach, Melt extrusion: from process to drug delivery technology, 54 EUR. J. OF PHARMACEUTICS AND BIOPHARMACEUTICS 107-17(2002) which is hereby incorporated by reference in its entirety. See also, e.g., U.S. Pat. Nos. 4,801,460; 5,456,923; 5,700,410; and 5,945,127.

The manufacturing of the solid dispersions of the present invention begins with the compounding of the therapeutic compound along with the solubilizer, optional plasticizer, and the carrier using melt extrusion to form an extrudate. The solubilizer, e.g., may be present in an amount from about 5% to about 40% by weight of the composition of the extrudate, e.g., from about 10% to about 35%, e.g., from about 25% to about 30%. Similarly, the therapeutic compound, may be present in an amount from about 0.01% to about 50% by weight of the composition of the extrudate, e.g., from about 5% to about 40%, e.g., from about 10% to about 20%. The heating and mixing of the therapeutic compound and the carrier to form extrudate is accomplished by the use of an extruder. The carrier, e.g., can be present in an amount from about 1% to about 99% by weight of the composition. Unlike granules made during a wet granulation process, the melt extrusion process of the present invention does not require a granulation fluid, for example, water, methanol, ethanol, isopropanol or acetone during the granulation process.

The extrudate is, for example, subsequently milled into granules which form the internal phase of the pharmaceutical composition. One of ordinary skill in the art will appreciate the necessary particle size of the granule that is necessary for the particular pharmaceutical composition being formulated. For example, suitable particle sizes, include those of less than equal to 1,000 μm, 750 μm, 500 μm or 250 μm. Alternatively, the extrudate can be directly molded into tablets, cut into multiparticles or processed into any other forms as known to one of ordinary skill in the art.

The resulting granules are, for example, particles of the therapeutic compound embedded, substantially embedded in, coated, continuously or discontinuously, by the release retardant.

The resulting granules are, for example, particles of the therapeutic compound coated or substantially coated by the granulation excipient, or alternatively, particles of the therapeutic compound embedded or substantially embedded with or within the granulation excipient.

Once the granules are obtained, the granules may be formulated into oral forms, e.g., solid oral dosage forms, such as tablets, pills, lozenges, caplets, capsules or sachets, by adding additional conventional excipients which comprise an external phase of the pharmaceutical composition. The external phase of the pharmaceutical composition can also comprise an additional therapeutic compound. Such solid oral dosage forms, e.g., are unit oral dosage forms. Examples of such excipients include, but are not limited to, release retardants, plasticizers, disintegrants, binders, lubricants, glidants, stabilizers, fillers and diluents. One of ordinary skill in the art may select one or more of the aforementioned excipients with respect to the particular desired properties of the solid oral dosage form by routine experimentation and without any undue burden. The amount of each excipient used may vary within ranges conventional in the art. The following references which are all hereby incorporated by reference discloses techniques and excipients used to formulate oral dosage forms. See *The Handbook of Pharmaceutical Excipients*, $4^{th}$ edition, Rowe et al., Eds., American Pharmaceuticals Association (2003); and *Remington: the Science and Practice of Pharmacy*, $20^{th}$ edition, Gennaro, Ed., Lippincott Williams & Wilkins (2003).

Examples of pharmaceutically acceptable disintegrants include, but are not limited to, starches; clays; celluloses; alginates; gums; cross-linked polymers, e.g., cross-linked polyvinyl pyrrolidone or crospovidone, e.g., POLYPLASDONE XL from International Specialty Products (Wayne, N.J.); cross-linked sodium carboxymethylcellulose or croscarmellose sodium, e.g., AC-DI-SOL from FMC; and cross-linked calcium carboxymethylcellulose; soy polysaccharides; and guar gum. The disintegrant may be present in an amount from about 0% to about 10% by weight of the composition. In one embodiment, the disintegrant is present in an amount from about 0.1% to about 1.5% by weight of composition.

Examples of pharmaceutically acceptable binders include, but are not limited to, starches; celluloses and derivatives thereof, for example, microcrystalline cellulose, e.g., AVICEL PH from FMC (Philadelphia, Pa.), hydroxypropyl cellulose hydroxylethyl cellulose and hydroxylpropylmethyl cellulose METHOCEL from Dow Chemical Corp. (Midland, Mich.); sucrose; dextrose; corn syrup; polysaccharides; and gelatin. The binder may be present in an amount from about 0% to about 50%, e.g., 10-40% by weight of the composition.

Examples of pharmaceutically acceptable lubricants and pharmaceutically acceptable glidants include, but are not limited to, colloidal silica, magnesium trisilicate, starches, talc, tribasic calcium phosphate, magnesium stearate, aluminum stearate, calcium stearate, magnesium carbonate, magnesium oxide, polyethylene glycol, powdered cellulose and microcrystalline cellulose. The lubricant may be present in an amount from about 0% to about 10% by weight of the composition. In one embodiment, the lubricant may be present in an amount from about 0.1% to about 1.5% by weight of composition. The glidant may be present in an amount from about 0.1% to about 10% by weight.

Examples of pharmaceutically acceptable fillers and pharmaceutically acceptable diluents include, but are not limited to, confectioner's sugar, compressible sugar, dextrates, dextrin, dextrose, lactose, mannitol, microcrystalline cellulose, powdered cellulose, sorbitol, sucrose and talc. The filler and/or diluent, e.g., may be present in an amount from about 15% to about 40% by weight of the composition.

The mixture is heated to a temperature(s) less than the melting temperature of the therapeutic compound, and that of the solubilizer. As the mixture is being heated, it is also being kneaded by the screw(s) of the extruder. The mixture is maintained at the elevated temperature and blended for a time sufficient to form a granulated product. After the mixture is conveyed down the entire length of the barrel, a granulated product (being the extrudate) is obtained, and the granulated mixture is cooled.

After cooling, the extrudate can be milled and subsequently screened through a sieve. The granules (which constitute the internal phase of the pharmaceutical composition) are then combined with solid oral dosage form excipients (the external phase of the pharmaceutical composition), i.e., fillers, binders, disintegrants, lubricants and etc. The combined mixture may be further blended, e.g., through a V-blender, and subsequently compressed or molded into a tablet, for example a monolithic tablet, or encapsulated by a capsule.

Once the tablets are obtained, they can be optionally coated with a functional or non-functional coating as known in the art. Examples of coating techniques include, but are not limited to, sugar coating, film coating, microencapsulation and compression coating. Types of coatings include, but are not limited to, enteric coatings, sustained release coatings, controlled-release coatings.

The utility of all the pharmaceutical compositions of the present invention may be observed in standard clinical tests in, for example, known indications of drug dosages giving therapeutically effective blood levels of the therapeutic compound; for example using dosages in the range of 2.5-250 mg of therapeutic compound per day for a 75 kg mammal, e.g., adult and in standard animal models.

The present invention provides a method of treatment of a subject suffering from a disease, condition or disorder treatable with a therapeutic compound comprising administering a therapeutically effective amount of a pharmaceutical composition of the present invention to a subject in need of such treatment.

The following examples are illustrative, but do not serve to limit the scope of the invention described herein. The examples are meant only to suggest a method of practicing the present invention.

An example of a poorly water soluble therapeutic compound appropriate for the present invention is midostaurin which is a protein Kinase C inhibitor. This crystalline compound has a high melting point of about 260° C., and the compound decomposes upon melting. Furthermore, the compound is light-sensitive and oxidizes.

TABLE 2

| Ingredient | Percentage (w/w) |
| --- | --- |
| midostaurin | 10% |
| polyvinyl pyrrolidone | 40% |
| poloxamer 188 | 40% |
| Sorbitol | 10% |
| Total | 100% |

The ingredients of Table 2 are weighed and placed into a mortar and pestle in which they are gently mixed for one minute forming a mixture. Subsequently the mixture is transferred to the feed section, or hopper, of a twin screw extruder. A suitable twin screw extruder is the Haake MiniLab Micro Compounds Product #557-2200 available from Thermo Electron Corp. (Waltham, Mass.). This extruder has a single zone has for mixing. The extruder is heated to a temperature of 150° C. The material travels in the extruder with a residence time of about two minutes.

The resulting extrudate is semisolid with an approximate temperature of 100°. To quickly solidify the extrudate, it is placed in a freezer. However, air-cooling can also be used to solidify the extrudate. Subsequently, the extrudate is milled and suitable for analytical testing.

Figure 2:
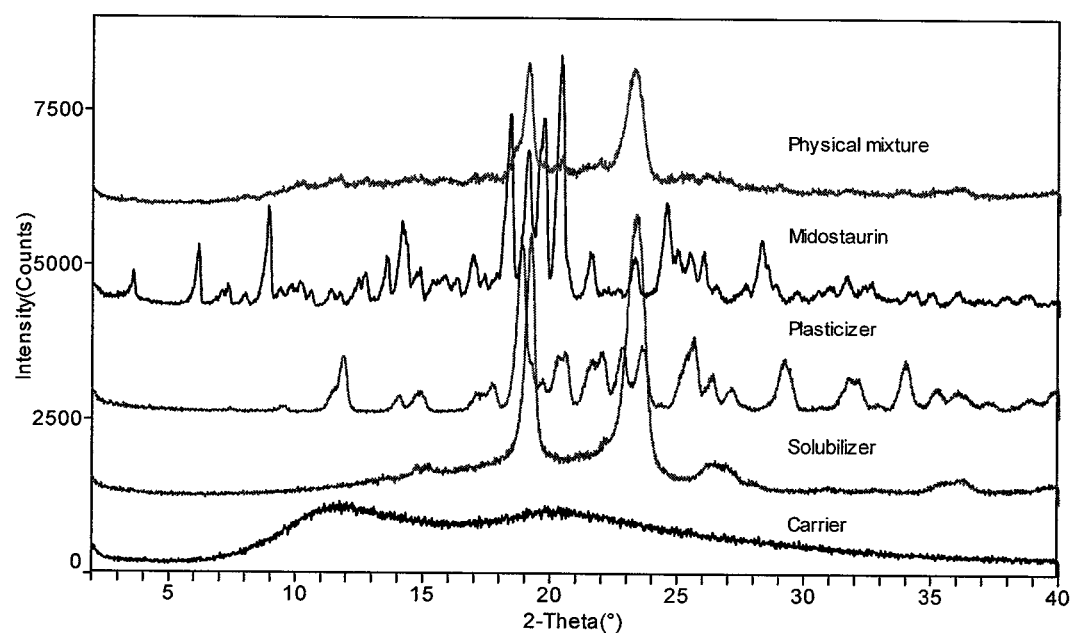
FIG. 2. depicts a chart showing the respective powder x-ray diffraction patterns for the individual constituents in Table 2 and the physical mixture thereof.

FIG. 1 shows two powder x-ray diffraction patterns of a physical mixture of the ingredients of Table 2 as compared to a solid dispersion produced by the inventive process of the present invention using the same ingredients. FIG. 2 provides a comparison in that the PXRD patterns of the individual ingredients are shown. FIG. 2 shows the physical mixture, midostaurin, plasticizer (i.e., sorbitol), solubilizer (i.e., poloxamer 188), and carrier (i.e., polyvinyl pyrrolidone). In the solid dispersion pattern of FIG. 1, the midostaurin is amorphous since there are no shark peaks. Instead there is a halo which shows formation of the amorphous therapeutic compound.

It is understood that while the present invention has been described in conjunction with the detailed description thereof that the foregoing description is intended to illustrate and not limit the scope of the invention, which is defined by the scope of the following claims. Other aspects, advantages and modifications are within the scope of the claims.

What is claimed:

1. A method for making a solid dispersion of a therapeutic compound, the method comprising the steps of:
combining crystalline midostaurin with a carrier, a solubilizing agent, and the plasticizer sorbitol to form a mixture;
processing said mixture in a single zone extruder while heating at a temperature of about 100° C. less than the degradation temperature of the crystalline midostaurin; and
extruding said mixture to form an extrudate, wherein said midostaurin in said extrudate is in an amorphous state.

2. The method of claim 1, wherein said solubilizing agent is a poloxamer.

3. The method of claim 2, wherein said poloxamer is poloxamer 188.

4. The method of claim 1, wherein said heating is from a temperature of 150° C. to 170° C.

5. The method of claim 1, wherein said solubilizing agent is present in said mixture from about 10% to about 40% by weight of the mixture.

6. The method of claim 1, further comprising the step of compressing said extrudate to form a solid oral dosage form.

* * * * *